United States Patent [19]

Pfeifer et al.

[11] 4,247,777
[45] Jan. 27, 1981

[54] OPERATING CONSOLE FOR AN X-RAY DIAGNOSTIC INSTALLATION

[75] Inventors: Rolf Pfeifer; Eike Matura, both of Erlangen, Fed. Rep. of Germany

[73] Assignee: Siemens Aktiengesellschaft, Berlin & Munich, Fed. Rep. of Germany

[21] Appl. No.: 902,807

[22] Filed: May 4, 1978

[30] Foreign Application Priority Data

Jun. 20, 1977 [DE] Fed. Rep. of Germany ... 7719261[U]

[51] Int. Cl.³ .......................... H05G 1/00; H05G 1/70
[52] U.S. Cl. .................................. 250/416 R; 250/402
[58] Field of Search ................... 250/416 R, 402, 408, 250/407

[56] References Cited

U.S. PATENT DOCUMENTS

| | | | |
|---|---|---|---|
| 4,037,107 | 7/1977 | Lutz et al. | 250/402 |
| 4,080,536 | 3/1978 | Brehin et al. | 250/407 |

FOREIGN PATENT DOCUMENTS 1439547  6/1976  United Kingdom ................. 250/416 R

OTHER PUBLICATIONS

*Standard Handbook for Electrical Engineer's*, ed. by Knowlton et al., eighth ed., McGraw Hill, 1949, pp. 2271-2272, 1148-1153.

*Primary Examiner*—Eli Lieberman
*Assistant Examiner*—T. N. Grigsby
*Attorney, Agent, or Firm*—Hill, Van Santen, Steadman, Chiara & Simpson

[57] ABSTRACT

The illustrated embodiment includes a selection device for the radiographic exposure values of each radiographic system, as well as a switching arrangement for connecting one of the radiographic systems in each instance to a common feed and control apparatus. The operating console is provided with representations of all associated radiographic systems. There is present for each radiographic system at least one signal lamp for the purpose of illuminating the representation of the radiographic system on the operating console, said signal lamp being a component of a monitoring device for monitoring the operational readiness and proper operation of the radiographic systems. It is possible to symbolically represent the path of rays of each radiographic system, and to associate with each radiation path symbol at least one signal lamp for the purpose of illumination which is likewise a component of the monitoring device.

2 Claims, 2 Drawing Figures

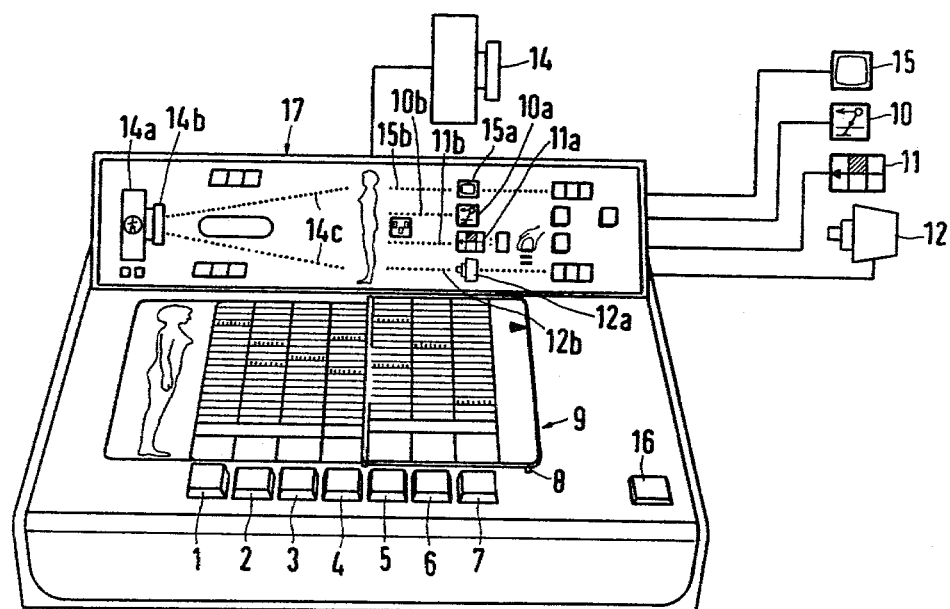
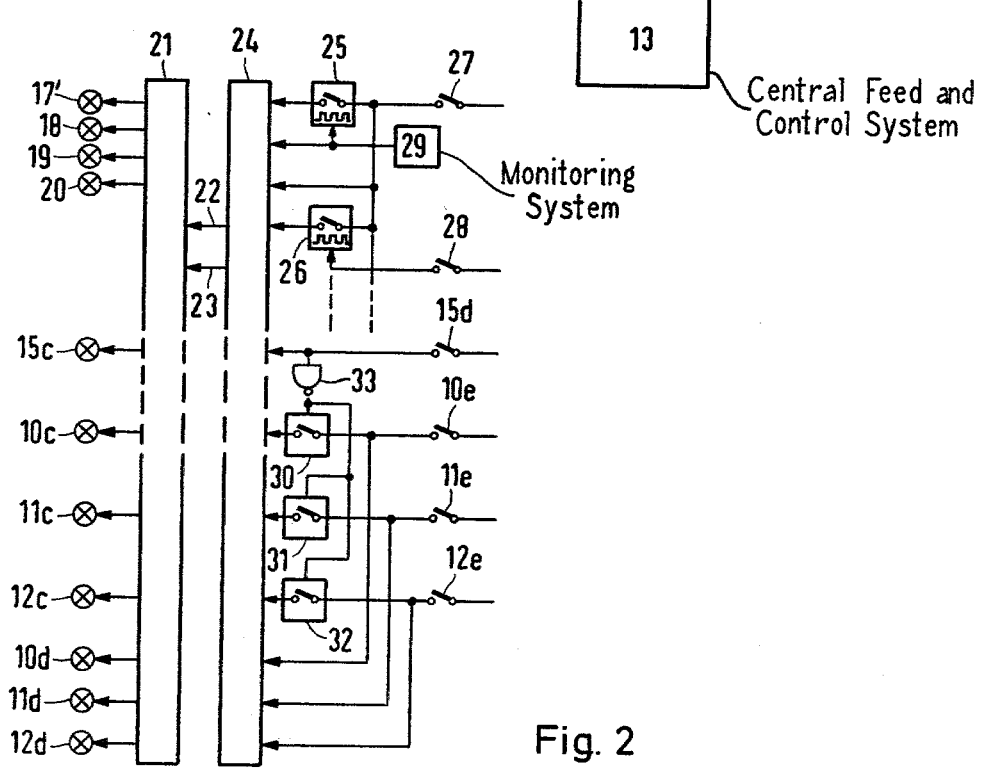

OPERATING CONSOLE FOR AN X-RAY DIAGNOSTIC INSTALLATION

BACKGROUND OF THE INVENTION

The invention relates to an operating console for an x-ray diagnostic installation comprising an x-ray tube and a plurality of radiographic systems, on which is arranged a selection device comprising switching means for adjusting the radiographic exposure values of each radiographic system, as well as a manually actuatable switching arrangement for connecting one of the radiographic systems in each instance to a common feed and control apparatus, and which operating console is provided with representations of the associated radiographic systems.

An operating panel or console of this type is described in U.S. Pat. No. 4,080,536. In the case of this operating console, it is not possible to monitor the operational readiness and the proper operation of the respectively selected radiographic system.

In the German Offenlegungsschrift No. 23 12 751, there is described an x-ray diagnostic installation comprising a plurality of radiographic systems selectively capable of connection to a common generator with which one operating console each is associated for the purpose of setting the radiographic exposure values and with which means are associated for connecting the associated x-ray tube to the generator and for starting further auxiliary apparatus. Each operating console here is provided with an indicator field comprising a signal lamp for the purpose of indicating the operational readiness and the proper operation of the associated radiographic system. In the case of this x-ray diagnostic system, one operating console is present for each radiographic system on which operating console accordingly, it is also possible to only monitor the respectively associated radiographic system. The plurality of operating consoles in the case of an x-ray diagnostic installation comprising an x-ray tube and a plurality of radiographic systems thus presents a great disruptive factor and is not capable of being monitored in its entirety.

SUMMARY OF THE INVENTION

The object underlying the invention consists in constructing an operating console of the type initially cited such that it is possible to monitor at a glance all associated radiographic systems with regard to operational readiness and proper operation.

In accordance with the invention, this object is achieved by virtue of the fact that at least one signal lamp is present for each radiographic system for the purpose of illuminating the representation of the radiographic system, said signal lamp being a component of the monitoring device for the operational readiness and proper operation of the radiographic systems. In the inventive operating console, the representations of all associated radiographic systems are illuminated by a corresponding number of signal lamps. Thus, the operational state of each radiographic system can be recognized in a particularly eye-catching manner by virtue of the signal lamps spatially associated with the representations.

An expedient further embodiment of the invention consists in that, for each radiographic system, the respective path of rays leading to the latter is symbolically represented, and that there is present for each radiation path symbol at least one signal lamp for illuminating the radiation path symbol which is likewise a component of the monitoring device. In the case of this further development, it is possible to recognize the transition from fluoroscopy to photography from the signal lamps spatially associated with the radiation path symbols.

The invention shall be explained in greater detail in the following on the basis of a sample embodiment illustrated in the accompanying sheet of drawings; and other objects, features and advantages will be apparent from this detailed disclosure and from the appended claims.

BRIEF DESCRIPTION OF THE DRAWINGS

FIG. 1 illustrates an operating console in accordance with the invention in conjunction with the associated x-ray diagnostic installation; and FIG. 2 is an illustration for the purpose of explaining the operating console according to FIG. 1.

DETAILED DESCRIPTION

The operating console illustrated in FIG. 1 exhibits seven organ keys 1 through 7 which render possible the selection of the radiographic exposure values of the respectively selected radiographic system in an organ-programmed fashion. To this end, one column each with the associated organs is selected via each of the organ keys 1 through 7. A human body recorded to the left of these columns serves the purpose of locating the respectively sought-for bodily part or organ. The bodily parts or organs associated with the organ keys 1 through 7 are recorded on panels 9 which can be turned over like the pages of a book. Each panel position thus corresponds to a specified radiographic system; i.e., the radiographic system is selected by turning over the panels 9. The automatic selection proceeds by means of a switching device 8 which is actuated when the panels 9 are turned over.

In the illustrated position of the panels 9, e.g. a tomographic apparatus 10 is selected as the recording system. Instead of tomographic apparatus 10, it is also possible to select a symbolically represented x-ray sighting device 11, or it is possible to select a cine camera 12 for indirect photographs of the output of an x-ray image intensifier.

In FIG. 1, a central feed and control apparatus 13 is additionally represented which feeds an x-ray tube 14 and controls the radiographic systems 10 through 12 as well as a video unit 15 for x-ray fluoroscopy in conjunction with a non-illustrated x-ray image intensifier.

In order to prepare x-ray photographs with a specified radiographic system, the organs or bodily parts corresponding to the radiographic system are brought into view by turning over the panels 9 disposed opposite the ogan keys 1 through 7, and, finally, the particular organ key of organ keys 1 through 7 which corresponds to the organ to be photographed is depressed. The radiographic system is automatically selected via the switching device 8 upon turning over the panels 9, and the photograph can be actuated by means of pressure exerted on a photographic trigger device 16.

The operating console in accordance with FIG. 1 manifests an indicator field 17 in which are provided a representation 14a of the x-ray tube 14, a representation 14b of the primary radiation diaphragm of the x-ray tube 14, a representation 14c of the incident x-radiation path, a representation of the patient, and representations 10a, 11a, 12a of the radiographic systems 10 through 12, as well as a representation 15a of the video unit 15. Lines 10b, 11b, 12b, 15b, as radiation path symbols, lead to the representations 10a, 11a, 12a, 15a. Representations 10a, 11a, 12a, 15a, and the lines 10b, 11b, 12b, 15b are applied on translucent material, and there are provided spatially behind said representations and lines, indicator lamps whose function shall be explained in further detail in conjunction with FIG. 2.

FIG. 2, only a portion of the indicator lamps; namely, indicator lamps 10c, 11c, 12c, 10d, 11d, 12d, and 15c are illustrated. In addition, indicator lamps 17' and 18 through 20 are illustrated. All indicator lamps are connected to a multiplexer receiver 21 which is connected via a data line 22 and a pulse line 23 to a multiplexer transmitter 24. There are connected to the inputs of the multiplexer transmitter 24 pulse generators 25, 26, switches 27, 28, a monitoring apparatus 29 for monitoring the loading of the x-ray tube, switches 30, 31, 32, which are controlled by an inversion stage 33 in dependence upon a fluoroscopy signal, as well as switches 10e, 11e, 12e, 15d.

If the operating location associated with the operating console is selected, switch 27 is closed and normally causes lamp 17' to light up continuously. Lamp 17' illuminates representation 14a of x-ray tube 14. If the monitoring apparatus 29 detects an overload on the part of the x-ray tube, it switches on the pulse generator 25, such that lamp 17' is made to blink. Simultaneously a lamp 18 is switched on which indicates the overload. Subsequent to selection of the working location; i.e., upon closing of switch 27, lamp 19 is also lit continuously which illuminates the tube-neck representation for x-ray tube 14. In addition, a lamp 20 emits light which, upon operational readiness and proper operation subsequent to the closure of switch 27, constantly illuminates representation 14b of the primary radiation diaphragm. If a malfunction is present; i.e., if the primary radiation diaphragm is closed, switch 28 is closed and switches on pulse generator 26 which effects a blinking of the lamp 20 and hence of representation 14b of the primary radiation diaphragm.

During a fluoroscopy operation, switch 15d is closed and switches on lamp 15c. Lamp 15c illuminates representations 15a and 15b. Corresponding to the radiographic system selected, one of the switches 10e, 11e, 12e, is closed for the purpose of preparing a photograph or a photographic series. Accordingly, one of the lamps 10d, 11d, 12d, emits light, and illuminates the corresponding representation 10a, 11a, 12a. If no fluoroscopy is effected; i.e., if switch 15d is opened, one of the lamps 10c, 11c, 12c also emits light and illuminates the corresponding line 10b, 11b, 12b. If, on the contrary, fluoroscopy is effected, this signal lamp is extinguished via inversion stage 33 and one of switches 30, 31, 32; i.e., in this case, none of the signal lamps 10c, 11c, 12c emits light, but only signal lamp 15c and one of signal lamps 10d, 11d, 12d.

Within the framework of the invention, it is also possible for additional signal lamps and associated control members to be present which illuminate corresponding representations in the indicator field 17. This is indicated by the broken lines in FIG. 2. However, it is essential that there be present, on an operating console for a plurality of radiographic systems, a representation of each radiographic system, which representation can be illuminated by at least one signal lamp in each instance, so that it is possible to recognize the operational readiness and the proper operation on the basis of the signal lamp.

It will be apparent that many modifications and variations may be effected without departing from the scope of the novel concepts and teachings of the present invention.

I claim as my invention:

1. In an x-ray diagnostic installation comprising an x-ray tube, a plurality of x-ray radiographic systems, and a central feed and control system for supplying the x-ray tube and controlling the x-ray radiographic systems, a unitary common operating console common to all of said x-ray radiographic systems, said common operating console including a manually actuatable switching arrangement for selectively connecting any one of said x-ray radiographic systems with said central feed and control system, and switching means for adjusting the radiographic exposure values for the selected x-ray radiographic system, said operating console having a display panel providing respective distinctive representations (10a, 11a, 12a) for identifying the respective x-ray radiographic systems, and having means comprising respective individual signal lamps (10d, 11d, 12d) for providing selective illumination of the respective distinctive representations on said display panel, and a monitoring device (FIG. 2) having means controlling the selective energization of the respective individual signal lamps (10d, 11d, 12d) in response to selection of the respective corresponding x-ray radiographic system by said manually actuatable switching arrangement, whereby the corresponding distinctive representation (10a, 11a, 12a) on the display panel is illuminated to visually signify which of the x-ray radiographic systems has been selected.

2. An operating console according to claim 1, characterized in that, for each x-ray radiographic system (10, 11, 12), the path of rays leading to said radiographic system is in each instance symbolically represented on said panel, said panel having for each radiation path symbol (10b, 11b, 12b) thereon at least one signal lamp (10c, 11c, 12c) for illuminating the radiation path symbol (10b, 11b, 12b) which is likewise a component of the monitoring device (FIG. 2).

* * * * *